United States Patent [19]

Shiff et al.

[11] Patent Number: 5,942,396
[45] Date of Patent: Aug. 24, 1999

[54] METHOD FOR IDENTIFYING INDIVIDUALS AT RISK FOR COLORECTAL NEOPLASIA BY QUANTIFYING NORMAL COLONIC MUCOSAL EPITHELIAL CELL APOPTOSIS

[75] Inventors: Steven J. Shiff, New York, N.Y.; Basil Rigas, Nashua, N.H.

[73] Assignee: The Rockefeller University, New York, N.Y.

[21] Appl. No.: 08/914,105

[22] Filed: Aug. 19, 1997

[51] Int. Cl.[6] .............................. C12Q 1/68; C12Q 1/00; G01N 33/574

[52] U.S. Cl. .................. 435/6; 435/4; 435/7.1; 435/7.21; 435/7.23; 435/29; 435/968

[58] Field of Search ..................... 435/4, 6, 7.1, 7.21, 435/7.23, 29, 968

[56] References Cited

U.S. PATENT DOCUMENTS

5,693,474   12/1997   Shay et al. ................................ 435/6

OTHER PUBLICATIONS

Akamatsu et al., 1996, Glycoconjugate J., 13:1021–9.
Arai and Kino et al., 1995, J. Pathol, 176:37–44.
Baretton et al., 1996, Cancer, 77:255–64.
Bedi et al., 1995, Cancer Research, 55:1811–6.
Boehringer Mannheim Corp. (1995) Product Catalog #: 1,399,861; 1,544,675; 1,585,045; 1,644,793; 1,684,795; 1,684,809; 1,774,425;.
Boersma et al., 1996, Cytometry, 24:123–30.
Browne et al., 1994, Int. J. Cancer, 59:56–64.
Clark et al. (1994) Oncogene 9:1767–73 (Abstract).
Einspahr et al., 1997, Cancer Epidemiology, Biomarkers & Prevention, 6:37–48.
Engeland et al., 1996, Cytometry., 24:131–9.
Erusalimsky et al., 1996, Anal. Biochem., 242:187–96.
Fairbairn et al., 1995, Mutation Res., 339:37–59.
Ferlini et al., 1996, Cytometry, 24:106–115.
Frankfurt et al., 1996, Exp. Cell Res. 226:387–97.
Frankfurt et al., 1997, Clinical Cancer Research, 3:465–71.
Garewal et al., 1996, Cancer Research, 56:1480–3.
Gavrieli et al., 1992, J. Cell. Biol., 119:493–501.
Hague et al., 1994, Oncogene, 9:3367–70.
Hall et al., 1994, J. Cell Science, 107:3569–77.
Hayashi, et al. 1996, Cancer Research, 56:4307–10.
Hawkins et al.,1997, Tumor Biology, 18:146–56.
Hirose et al., 1996, Jpn. J. Cancer Res., 87:575–82.
Lu et al., 1996, Anal. Biochem., 235:227–33.
Morin et al., 1996, Proc. Natl. Acad. Sci., 93:7950–4.
Moss et al., 1996, Gastroenterology, 111:1425–32.
Nakamura et al., 1995, Pathol Int, 45:721–8.
Nassauw et al., 1996, J. Histochem. Cytochem., 44:183–5.
Payne et al., 1995, Ultrastruct. Pathol., 19:221–48.
Pereira et al. (1997) World J. Surg. 21:210–3 (Medline Abst. 15406860).
Phelouzat et al., 1996, Biotechniques, 21:214–6.
R & D System, Apoptosis Detection Kit, Catalog Number: Knx50.
Salgame et al., 1997, Nucleic Acids Res., 25:680–1.
Sinicrope et al., 1996, Clinic Cancer Research, 2:1999–2006.
Strater et al., 1995, Gut 37(6):819–825.
Tatebe et al., 1996, Int. J. Cancer, 65:173–77.
Trosko et al., 1995, Stem Cells, 13:231–9.
Tsujitani et al., Cancer Supplement, 1996, 77:1711–6.
Wallet et al., 1996, Cytometry, 25:263–70.
Ward et al., 1997, Cancer, 79:1106–13.
Werner et al., 1993, Clinic Chimica Acta, 217:39–55.
Winawer et al., 1997,Gastroenterology, 112:594–642.
Zamai et al., 1996, Cytometry, 23:303–11.
Zhu et al. (1997) Anal. Biochem. 246:155–8.
Langlois et al. J. Pathol. vol. 182, pp. 392–397, 1997.

*Primary Examiner*—Leon B. Lankford, Jr.
*Assistant Examiner*—Christopher R. Tate
*Attorney, Agent, or Firm*—Klauber & Jackson

[57] ABSTRACT

Methods are described for determining in individuals with or without a prior history of colorectal neoplasia whether the individual has had, has, or has a risk of developing colorectal neoplasia. The method involves an assessment of the extent of apoptosis, or programmed cell death, in a colorectal biopsy specimen. Any of numerous methods to measure the extent of apoptosis in the sample is contemplated. For example, normal-appearing mucosa from the distal colon and/or rectum may be obtained from individuals undergoing screening procedures for colorectal cancer. The tissue is subjected to a method that assesses apoptosis, for example, by the extent of broken DNA ends in the nuclei of the cells in the specimen. The extent of apoptosis is expressed as a numerical ratio and indicates the possibility that an individual patient has a premalignant or malignant lesion in his or her colon or the risk for the development of a colorectal neoplasm in the future. Furthermore, the method has utility in determining whether a patient with, or at risk of developing, colorectal neoplasia is responding to prevention or intervention therapy.

2 Claims, 2 Drawing Sheets

METHOD FOR IDENTIFYING INDIVIDUALS AT RISK FOR COLORECTAL NEOPLASIA BY QUANTIFYING NORMAL COLONIC MUCOSAL EPITHELIAL CELL APOPTOSIS

FIELD OF THE INVENTION

This invention relates to methods for identifying individuals who have had or presently have colorectal neoplasia or are at risk for the development of colorectal cancer.

BACKGROUND OF THE INVENTION

Currently, the best means of preventing colorectal cancer is through early detection of pre-neoplastic lesions in the colon through various non-invasive or invasive screening techniques. For example, all individuals age 50 and above in the United States are recommended to undergo some form of colorectal cancer screening on a regular basis. Those with personal or family histories that suggest a greater risk for the development of this problem should be screened at earlier ages and more intensively. However, the earliest recognizable abnormality that clearly indicates an increased risk for colorectal cancer development is the adenoma. Not only are individuals with adenomas at increased risk but with appropriate surveillance and preventive maneuvers, these persons have the greatest chances of benefiting from preventive strategies to inhibit the development of a malignancy. Thus, these individuals are ideal candidates for dietary or pharmacological interventions aimed at further reducing their risk.

Screening techniques have their limitations: 1) they require repetitive application even in individuals who are at only marginally increased risk for colon cancer (i.e., because of advanced age alone); and 2) the time interval between development of recurrent polyps (or a first polyp after a normal index endoscopic examination) or other pre-neoplastic lesions is long, making these macroscopic structural changes slow and inefficient biomarkers for risk assessment. For example, an individual at 50 years of age with a normal colonoscopy still may be at risk for colon cancer development and requires continued periodic screening for this problem. Furthermore, this individual may or may not benefit from chemopreventive intervention. A simple solution is to accept that all individuals are candidates for screening programs and chemopreventive interventions. However, in practice, this is: a) technically impossible; b) associated with potentially excessive risk compared to the benefits obtained; and c) is likely too expensive to be worthwhile. Thus, the ability to predict definitively whether an individual is at increased risk for the development of colon cancer would be a great advance that would target those in need of intervention and, therefore, save lives and reduce health care expenses.

Apoptosis is a process whereby cells die in a characteristic, controlled manner in response to specific stimuli and according to an intrinsic genetic program. Interference in the process of apoptosis, therefore, is believed to be important for the development of neoplasia. For example, the mechanism of induction of neoplasia by the protooncogene bcl-2 is believed to reside specifically in the inhibition of apoptosis (see Baretton et al., 1996, Cancer 77:255–264). Certain carcinogens may induce neoplasia by interfering directly with apoptosis (see, for example, Hayashi et al., 1996, Cancer Research 56:4307–4310).

In the mammalian gastrointestinal tract, apoptosis appears to be the process principally regulating cell loss (Hall et al., 1994, J. Cell Science 107:3569–3577). Recent reports, for example, Tsujitani et al. (1996, Cancer 77:1711–1716) claim that increased apoptosis is characteristic of colorectal neoplasia. Morin et al. (1996, Proc. Nat. Acad. Sci. U.S.A. 93:7950–7954) suggested that apoptosis plays a role in both advanced colorectal tumors but also in the earliest stages of neoplasia. Arai and Kino (1995, J. Pathol. 176:37–44) report that reduced prerentage of apoptotic cells in human colorectal tissue may lead to neoplasia. These conflicting reports on the level of apoptosis in relation to neoplasia may relate to the stage of neoplasia and the location from which the biopsy is taken.

Methods for the measurement of apoptosis in a cellular or tissue sample have been described. Numerous methods have been proposed in the literature and commercial kits exists for measurement of apoptosis. A quantitative measure of apoptosis in a cellular or tissue sample can be obtained by determining the ratio of the number of apoptotic cells in the sample to the total number of cells in the sample, the ratio being referred to as the apoptotic index. Morphologically, apoptotic cells display nuclear chromatin condensation, compactness of cytoplasmic organelles, and the appearance of pedunculated protuberances on the cell surface. DNA fragmentation characteristic of apoptotic cells can be identified by isolating nuclear DNA and analyzing it using gel electrophoresis to identify strand breakage. Using flow cytometry on cells stained with a specific DNA stain such as propidium iodide, the percent of apoptotic cells can be assessed by counting the number of cells in a sample with a DNA content typical of apoptotic cells. Histologically, apoptotic cells can be identified after staining by the terminal deoxynucleotidyl transferase dUTP-biotin nick end labeling (TUNEL) method, or a modification thereof, which labels fragmented DNA. Biotin-dUTP added to DNA is detected with avidin-peroxidase or other well-known methods.

Methods for assessing risk of development of colorectal neoplasia based upon assessment of apoptosis from a biopsy specimen have been described, but such methods have relied on in vitro cultivation of such cells with or without an additional treatment of the cells with agents in order to assess apoptosis. For example, Bedi et al. (1995, Cancer Research 55:1811–1816) cultivate colorectal epithelial cells in vitro prior to performing an assay for apoptosis. Garewal et al. (1996, Cancer Research 56:1480–1483) measure the ability for bile acids to induce apoptosis in vitro in colorectal mucosal cells. Payne et al. (1995, Ultrastruct. Pathol. 19:221–248) suggested that a resistance-to-apoptosis bioassay may prove useful as a biomarker for individuals at risk for colon cancer, as they proposed that the presence of bile salts that accompany a high-fat diet may select for apoptosis-resistant epithelial cells in the colon. Such in vitro methods and bioassays are cumbersome. Notwithstanding the skepticism proposed by Einspahr et al. (1997, Cancer Epidemiology, Biomarkers & Prevention 6:37–48) who surmised that quantitation of apoptotic cells within colonic crypts will be difficult, there exists a need for a simple, rapid method for assessing apoptosis directly from colorectal biopsy specimens to determine whether an individual has or has had colorectal neoplasia or has a risk for the development of colorectal neoplasia. Furthermore, there exists a need to identify individuals with or at risk for colorectal neoplasia who are or will be-responsive to prevention or intervention, whether by drug therapy or dietary modification, by monitoring the change in the extent of apoptosis in a biopsy specimen obtained at an interval or intervals after the individual has initiated prevention or intervention therapy.

SUMMARY OF THE INVENTION

The present invention generally contemplates a method for determining whether an individual with or without a prior history of colorectal neoplasia has had or presently has colorectal neoplasia, or is at risk for the development of colorectal neoplasia, by analyzing at least a part of a biopsy sample from the individual for evidence of apoptosis or DNA fragmentation. The extent of apoptosis or DNA fragmentation in a sample can take the form of a ratio of the number of such cells that are apoptotic or are displaying DNA fragmentation in the mucosal crypt or in one of its subdivisions or compartments to the total number of cells in the sample. The colorectal neoplasia or risk of colorectal neoplasia to be determined by this method includes colorectal adenoma and colorectal adenocarcinoma.

A further embodiment of the present invention comprises a method for determining whether an individual would be a candidate for preventive measures directed at colorectal neoplasms, by analyzing at least a part of a biopsy sample from an individual for evidence of apoptosis or DNA fragmentation as described above. Such contemplated preventive measures include surgery, administration of chemopreventive agents, diet modification, and the administration of chemotherapeutic agents. Furthermore, the present invention may be used to determine whether an individual with or at risk for the development of colorectal neoplasia is responding or may be responsive to preventive or intervention therapy, such as drug therapy or dietary modification, by measuring the change in extent of apoptosis in a colonic biopsy sample taken at an interval after initiation of prevention or intervention therapy.

The present invention further embodies a method for identifying candidates for medical procedures directed toward diagnosing and preventing colorectal neoplasia, by analyzing at least a part of a biopsy sample from an individual for evidence of apoptosis or DNA fragmentation as described above. The medical procedure may be colonoscopy, sigmoidoscopy, and the determination of colorectal tumor markers.

The present invention contemplates any one or a combinations of procedures known in the literature for analysis of apoptosis or DNA fragmentation in a cellular sample, for example, electron microscopic, light microscopic, histologic, ELISA, spectrophotometric, spectrofluorometric, radioisotopic, flow cytometric, and other methods. A preferred method is the TdT-mediated dUTP biotin nick end labeling (TUNEL) methodology.

In one embodiment, the invention describes a method of identifying individuals who have a colorectal neoplasm, comprising:
   a) detecting colonic cells that are either apoptotic or display DNA fragmentation; and
   b) determining the ratio of the number of such cells in the mucosal crypt or in one of its subdivisions or compartments to the total number of cells.

The present invention further describes a method for determining whether an individual with or without a prior history of colorectal neoplasia has had or presently has colorectal neoplasia or is at risk for the development of colorectal neoplasia, comprising:
   1) Obtaining a small piece of colorectal mucosa, as for example, by an endoscopic, sigmoidoscopic, or anoscopic biopsy, or by any other suitable means; and
   2) Detecting the ratio of apoptotic cells or of cells that have an increased amount of broken DNA ends to the total number of cells; such detection can be accomplished either by the TdT-mediated dUTP biotin nick end labeling (TUNEL) methodology or any other methodology that assesses apoptosis; and
   3) Comparing the result obtained from the procedure described in 2) to a databank that includes the corresponding ratios of comparable normal individuals and identifying those with a ratio beyond a certain level as being at increased risk for the development of colorectal neoplasia.

As a result of the assessment of apoptosis in a sample from a patient, a course of action may be recommended and carried out by the physician, including but not limited to surgery, dietary mpodification, and chemotherapeutic or chemopreventive measures.

The methods described in the present invention may be used in combination with other methods for establishing the history, presence, or risk of colorectal neoplasia, such as biomarkers of neoplasia.

An advantage of the methodology described herein for detection of colorectal neoplasia or risk thereof is that it can be minimally invasive, in that it requires visualization of the lowermost portion of the colorectum (i.e., via anoscopy or sigmoidoscopy). This is much less bothersome and poses less risk to the patient compared with either full sigmoidoscopy or colonoscopy.

A further object and advantage of the present invention is that the assessment of risk of colorectal neoplasia can be performed on a biopsy specimen directly and without the need to place the biopsy specimen in culture or to apply agents to the cells in culture in order to assess apoptosis. Various histologic, microscopic, and spectrophotometric methods are provided to assess the degree of apoptosis in the biopsy specimen.

Other objects and advantages will become apparent to those skilled in the art from a consideration of the ensuing detailed description in conjunction with the following illustrative drawings.

DETAILED DESCRIPTION OF THE INVENTION

Figure 1:
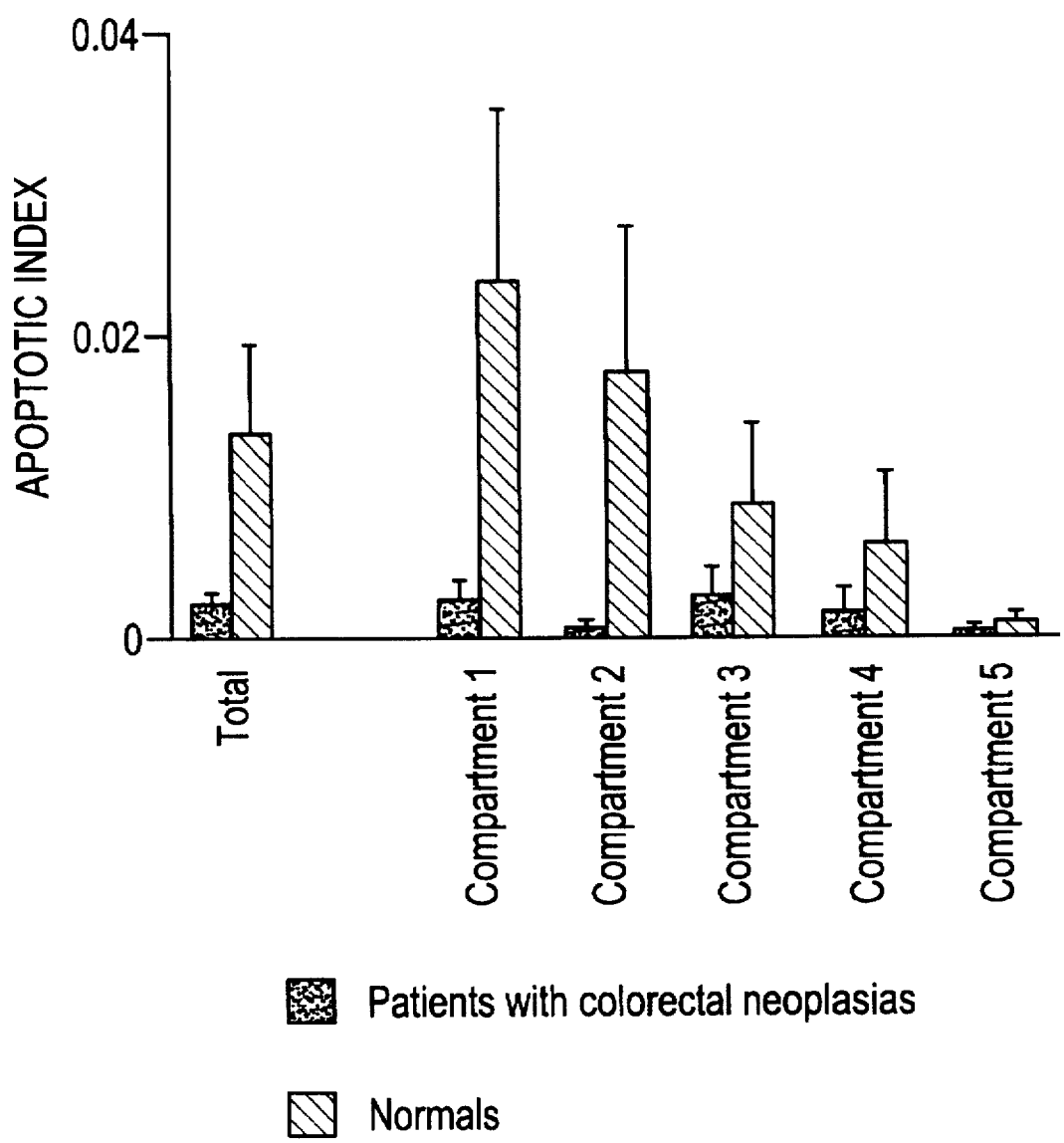
FIG. 1 shows the apoptotic index (AI) of normal controls and patients with a history of colonic neoplasia. The bars represent the mean values of the AI for the entire crypt (Total) and its compartments (Compartment 1–5) for each group. The vertical lines above the bars represent the SEM.

The present invention generally contemplates a method for determining whether an individual with or without a prior history of colorectal neoplasia has had or presently has colorectal neoplasia or is at risk for the development of colorectal neoplasia, by analyzing at least a part of a biopsy sample from the individual for the extent of apoptosis or DNA fragmentation. The extent of apoptosis in the flat mucosa of the colon is lower in certain portions along the crypt-villus axis of the colonic crypt, the basic structural unit of the colonic epithelium, in subjects who have or had a history of colorectal neoplasia. Therefore, by measurement of the extent of apoptosis in the colon of a particular person it is possible to make a recommendation regarding screening and chemopreventive intervention that is not possible at this point in time with conventional invasive or noninvasive screening methods.

The extent of apoptosis or DNA fragmentation in a sample can take the form of a ratio, or the percentage of such cells that are apoptotic or are displaying DNA fragmentation in the mucosal crypt or in one of its subdivisions or compartments, to the total number of cells. The possibility of or risk of colorectal neoplasia to be determined by this method includes colorectal adenoma and colorectal adenocarcinoma.

The present invention further embodies a method for identifying candidates for medical procedures directed toward diagnosing and preventing colorectal neoplasia, by analyzing at least a part of a biopsy sample from an individual for evidence of apoptosis or DNA fragmentation as described above. The medical procedure may be colonoscopy, sigmoidoscopy, and the determination of colorectal tumor markers.

As a result of the assessment of apoptosis, appropriate therapy may be recommended, including surgery, dietary modification, and administration of chemopreventive agents or chemotherapy. Furthermore, another aspect of the present invention is to monitor the responsiveness of a patient with or at risk for the development of colorectal neoplasia to prevention or intervention therapy or dietary modification, whereby the change in extent of apoptosis in a colonic biopsy is determined after the initiation of the therapy of dietary modification. In this manner, the responsiveness of the patient to the particular therapeutic regimen may be assessed by a change in the apoptotic index: a positive response indicated by relatively more apoptotic cells, and a lack of response by no change or a decrease in the AI. The change in response may indicate that the therapeutic regimen should be continued or changed. These data are critical for managing the disease as well as ensuring that chemopreventive measures are effective at reducing the risk.

The present invention contemplates any one or combinations of procedures known in the literature for analysis of apoptosis or DNA fragmentation in a cellular or tissue sample, for example, electron microscopic, light microscopic, histologic, ELISA, spectrophotometric, spectrofluorometric, radioisotopic, flow cytometric, and other methods. Based on any one or combination of these procedures, a ratio between apoptotic cells and total number of cells is determined, and compared to a predetermined range of values determined previously from biopsies using the various methods for measuring apoptosis, to determine whether the patient providing the sample is normal, has had or presently has, or is at risk for the development of, colorectal adenoma or colorectal adenocarcinoma.

Electron microscopic methods on colorectal biopsies suitably prepared for electron microscopic evaluation assess the extent and degree of nuclear chromatin condensation, compactness of cytoplasmic organelles, and appearance of pedunculated cell surface protuberances. Light microscopic methods include the identification of apoptotic bodies. Histological evaluation includes the processing of the sample for the TUNEL method (see below) to label fragmented DNA. The TUNEL method was originally described by Gavrieli et al. (1992, *J. Cell. Biol.* 119:493–501) as an in-situ histologic method to identify by microscopy apoptotic cells. Electrophoretic methods include the isolation of cellular DNA and separation by gel electrophoresis to determine the extent of DNA fragmentation; apoptotic cell DNA displays a characteristic laddering of multiples of 180 bp fragments. Flow cytometric methods include the use of DNA stains, such as propidium iodide, to determine by automated means the percent of cells with a quantity of DNA below a specific and characteristically apoptotic value.

Manual, semiautomated, and automated methods are also contemplated to assess the extent of apoptosis in a sample. Quantitation of DNA fragmentation by a modification of the TUNEL assay providing a spectrophotometric, spectrophotofluorimetric, or radioisotopic readout is contemplated, together with a method to assess the total amount of DNA or number of cells in the sample, for example by protein or DNA calorimetric assay or absorbance in the appropriate ultraviolet spectrum indicative of the quantity of DNA or protein present in the sample. The methods are all well-described in the literature and are incorporated herein by reference.

The present invention may be used in combination with other methods to assess the presence of colorectal neoplasia, including tumor markers or biomarkers, such as the proliferation potential assessed by staining tissues samples or cells derived from such samples, for proliferating cell nuclear antigen (PCNA) or Ki-67 antigen, or other biomarkers.

Other methods for assessing apoptosis have been described, and are summarized in the following table.

| Reference | Summary of Methodology |
| --- | --- |
| Frankfurt et al., 1996, Exp. Cell Res. 226:387–397. | Monoclonal antibody to single-stranded DNA by immunohistochemistry |
| Nassauw et al., 1996, J. Histochem. Cytochem. 44:183–185. | In situ DNA nick end labeling using immunogold reagents |
| Phelouzat et al., 1996, Biotechniques 21:214–216. | Chemiluminescent detection of fragmented DNA using the Boehringer Mannheim Corporation DIG Luminescent Detection Kit |
| Lu et al., 1996, Anal. Biochem. 235:227–233. | Filter elution assay to simultaneously detect DNA double strand breaks and single strand breaks |
| Boersma et al., 1996, Cytometry 24: 123–130. | Fluorescein-conjugated annexin V binding to membranes of apoptotic cells |
| Akamatsu et al., 1996, Glycoconjugate Journal 13:1021–1020 | Measure increased levels of $\alpha(1,3)$fucosyltransferase activity characteristic of apoptotic cells. |
| Salgame et al., 1997, Nucleic Acids Res. 25:680–681. | Double monoclonal sandwich ELISA for nucleosomes released into the cytoplasm, typical of apoptotic cells. |

-continued

| Reference | Summary of Methodology |
| --- | --- |
| Boehringer Mannheim Corp. | Photometric enzyme immunoassay for cytoplasmic histone-associated DNA fragments induced by apoptosis, using antibodies to histone and DNA. |
| R & D Systems | Apoptosis Detection Kit (flow cytometry) to detect percentage of cells undergoing apoptosis, based on binding of fluorescein-conjugated annexin V and exclusion of propidium iodide. |

The above list is intended to be illustrative, but not restrictive, of the various apoptosis assays that are presently available that may be used in the present invention in order to assess risk of neoplasia. In the practice of the present invention, the apoptotic index (AI) of the colonic mucosa of a patient is determined in a biopsy sample from the patient. The AI is determined by any of a number of well-known methods such as those described above. The AI value from the patient is compared to a previously established range of normal and abnormal AI values, and the patient may be classified as having a normal or abnormal AI value. The following non-limiting example is indicative of one such embodiment of the present invention.

EXAMPLE

Colorectal tissue is obtained by endoscopic biopsy in which a biopsy forceps inserted through a rigid or flexible endoscope resects a small (e.g. 3 mm×5 mm-sized) fragment of colorectal mucosal tissue. This tissue is then appropriately preserved, as for example, by immersion into 10% buffered formalin for an optimal duration, as for example, 12–24 hr. The preserved tissue may then be embedded in the appropriate material such as, for example, paraffin. The preserved tissue specimens are cut into slices of the appropriate thickness ranging for example between 0.9–5 μm with a microtome and placed on a microscope slide; charged or coated microscope slides are a preferred type of slide surface. In a preferred approach, paraffin-embedded specimens are de-paraffinized for 30 min at 60° C. in an oven, then dipped in xylene twice for 5 min and then 80 times in 100% ethanol. Endogenous peroxidase activity is quenched by applying 2.1% $H_2O_2$/93% methanol (v/v) to the samples for 15 min at room temperature. Specimens are then washed once in 100% ethanol, twice with 95% ethanol, and twice with distilled water.

Nuclear proteins are hydrolyzed by bathing the section with proteinase K 20 μg/ml in 10 mM Tris-HCl (pH=8) for 12–15 min at room temperature after a 5 min pre-incubation at room temperature with Tris-HCl (pH 8) alone.

In preparation for labeling the DNA nicks, the tissues are incubated with buffer (3 mM Tris-HCl pH 7.2, 14 mM sodium cacodylate and 0.1 mM cobalt chloride) for 5 min. The sections are then incubated with 50 μl of this buffer containing up to 15 pmole/μl biotinylated-dUTP and 0.3 U/μl terminal deoxytransferase (TdT) enzyme at 37° C. for 1 hr in a humid chamber. This nick end-labeling reaction is terminated by washing the slides with 2X SSC (0.3 M NaCl, 0.03 M NaCitrate pH=7.0), followed sequentially by 3 washes with distilled water and one with 1X Phosphate buffered saline (PBS)/1% Tween-20. Tissue specimens are then incubated for 10 min at room temperature with 2% bovine serum albumin (BSA) dissolved in 1X PBS with additional normal horse serum diluted 1:200 (v/v) and then washed with several changes of PBS/1% Tween-20. The secondary detection agent, extra avidin peroxidase (EAP) is added at 0.01 mg/ml in 1X PBS/1% BSA/0.5M NaCl to the sections for 30 min at 37° C. in a humid chamber.

After several serial washes with 1X PBS/1% Tween-20, nuclear peroxidase activity is detected as a brown coloration by treatment with di-amino benzidine (DAB) at room temperature. Afterward, the slides are washed with several changes of distilled water and counterstained with either 0.25% alcian blue/0.25% methyl green or filtered Harris hematoxylin or other suitable reagent. Finally, after additional washes with distilled water, the samples are dehydrated with progressively increased concentrations of ethanol followed by immersion in xylene. Samples are covered with mounting solution and cover slips and evaluated by light, fluorescent, or other suitable type of microscopy.

Quantitative analysis of the extent of apoptosis in the sample can be performed in several ways, for example, by visual examination of the slide through the microscope or by an automated image analysis system. Through these or other means, one or both of the following two measurements are made: 1) the percentage or ratio of apoptotic cells or those with DNA fragmentation in the colorectal mucosal crypts to the total number of cells; or 2) the number of apoptotic cells or those with DNA fragmentation along the longitudinal axis of the crypts divided into 5 equally divide4d zones along the surface of the colonic mucosa.

Quantification can be done as follows: the stained slide is scanned to determine the location of full-length crypts. These are defined as crypts whose entire extent is included within the specimen being examined. Positively-stained cells (i.e., apoptotic cells or those whose nuclei contain DNA breaks) and cells whose nuclei in the crypts are not histochemically stained-positive are counted in each crypt column. The number of positively-stained cells compared to the total number of cells in one-half of a crypt column (hemicrypt) is expressed as a ratio called the apoptotic index (AI=[number of positive nuclei]/[number of total nuclei]). The apoptotic index within each of 5 equally divided zones along the longitudinal axis of the crypt is also determined. The total number of nuclei in the hemicrypt (x) is divided by 5. Positively-stained nuclei in each x/5 groups of cells is divided by x/5 to yield the AI of each of the compartments. Compartment 1 is defined as the one closest to the base of the crypt and Compartment 5 is defined as the one closest to the lumenal surface. The AI of the entire hemicrypt and in each of the five zones are the relevant numerical data derived from this method. The surface is also counted and the AI determined.

Utilizing this method 19 individuals were evaluated. Ten of them were normal, had no personal or family history of colorectal neoplasia and had a normal colonoscopy at the time the tissue sample was taken for analysis by this invention. Nine others had a history of colorectal neoplasia including benign adenomatous polyps in 8 of them and one had a history of having a colon adenocarcinoma. FIG. 1 shows that the apoptotic index of patients with a history of colorectal neoplasia is lower than that of normal patients, and that this difference diminishes as one proceeds from compartment 1 to compartment 5. Compartment 2 shows a prominent difference in mean values. The AI values from compartments 1 and 2, and the total AI values from these patients are presented in the following table:

Apoptotic Indices (AI) of normal individuals (A through J) and those with (1 through 8) a history of colorectal neoplasia, and one patient (AA) with a history of colon cancer. AI data includes total and that for compartments 1 and 2.

| Pa-tient | Total | Comp. 1 | Comp. 2 | Pa-tient | Total | Comp. 1 | Comp. 2 |
|---|---|---|---|---|---|---|---|
| A | 0.0035 | 0.0047 | 0.0029 | 1 | 0.0000 | 0.0000 | 0.0000 |
| B | 0.0021 | 0.0022 | 0.0042 | 2 | 0.0000 | 0.0000 | 0.0000 |
| C | 0.0130 | 0.0320 | 0.0120 | 3 | 0.0060 | 0.0056 | 0.0000 |
| D | 0.0150 | 0.0310 | 0.0240 | 4 | 0.0000 | 0.0000 | 0.0000 |
| E | 0.0000 | 0.0000 | 0.0000 | 5 | 0.0065 | 0.0000 | 0.0000 |
| F | 0.0015 | 0.0078 | 0.0078 | 6 | 0.0028 | 0.0022 | 0.0024 |
| G | 0.0008 | 0.0000 | 0.0000 | 7 | 0.0022 | 6.0110 | 0.0000 |
| H | 0.0640 | 0.1190 | 0.1010 | 8 | 0.0026 | 0.0048 | 0.0043 |
| I | 0.0068 | 0.0120 | 0.0140 | | | | |
| J | 0.0076 | 0.0270 | 0.0094 | AA | 0.0000 | 0.0000 | 0.0000 |

Figure 2A:
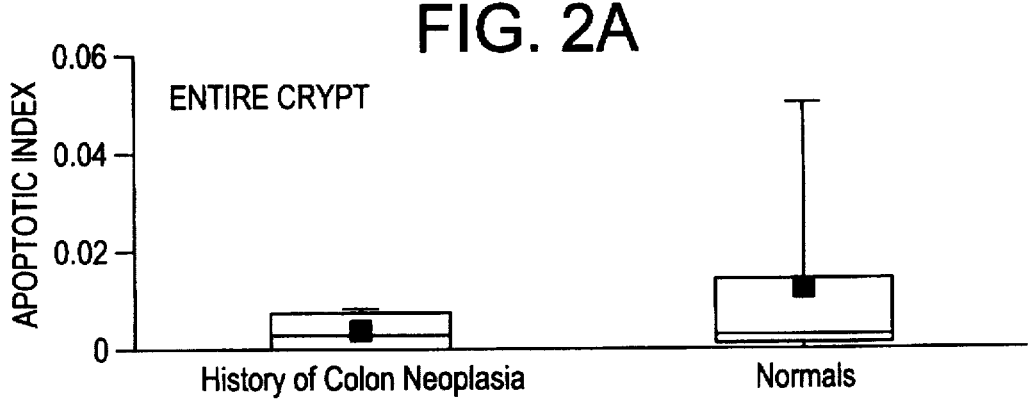
FIG. 2 is a box plot of the apoptotic index (AI) of two study groups: those with a history of colon neoplasia and normal controls. The small dark square represents the mean value for the AI for each group. The horizontal line traversing each box represents the median value of the AI, the top and bottom limits of the boxes represent the 75th and 25th percentile values of the AI respectively. The top and bottom of the vertical lines represent the 90th and 10th percentile values of the AI, respectively.
Figure 2B:
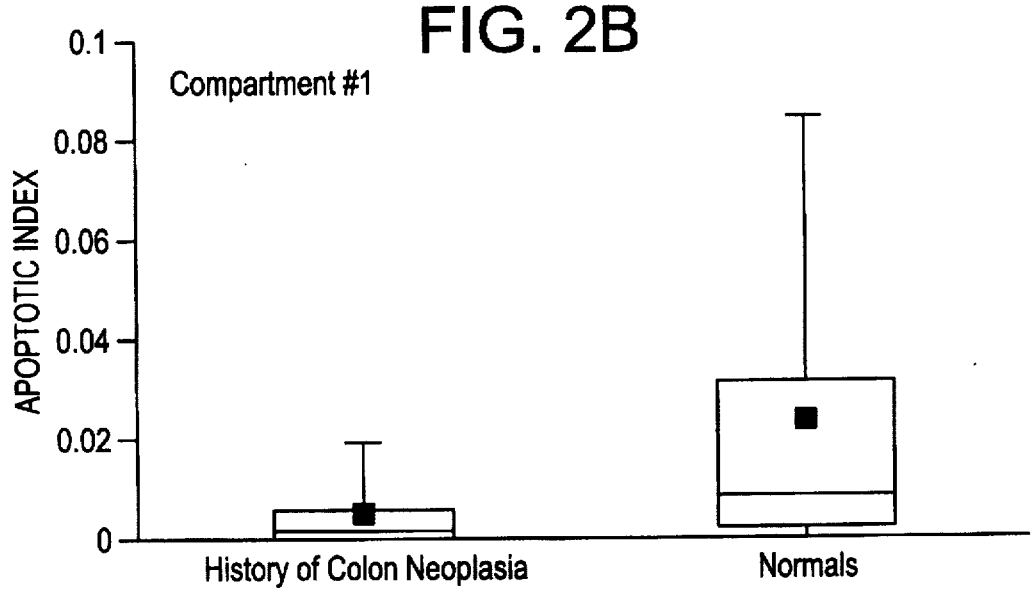
Figure 2C:
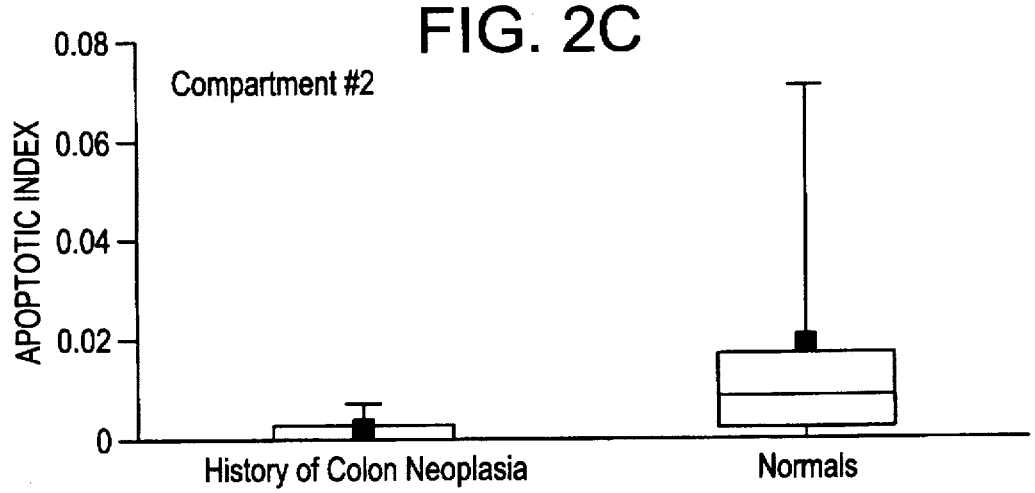

Compared to normal individuals (A-J), the percentage of cell exhibiting apoptosis or DNA fragmentation in the colorectal crypts was diminished in individuals with a history of colorectal neoplasia (patients 1–8). A more detailed plot of the mean total data and that of compartments 1 and 2 are shown in FIG. 2. In this box plot, the small dark square represents the mean value for the AI for each group. The horizontal line traversing each box represents the median value of the AI, the top and bottom limits of the boxes represent the 75th and 25th percentile values of the AI respectively. The top and bottom of the vertical lines represent the 90th and 10th percentile values of the AI, respectively.

It may be seen from the presentation of data in FIG. 2 that normal individuals whose AI values fall at the low end of the range, which are in proximity of the range of the patients with a history of colorectal neoplasia, are those patients who either had or have colorectal neoplasia (and hence misclassified as "normal"), or more likely, are at risk for the development of colorectal neoplasia. The one patient with a history of colorectal cancer (AA) had an AI of zero. Several individuals who were in the normal category had AI values within the range of the patients with colorectal neoplasia, such as individuals B, F, and G. Normal individual E had an AI of zero. Based on these data, these individuals may be suspected of having had, presently having, or having a risk for developing colorectal neoplasia. Because these normal individuals are not known to have had or presently have colorectal neoplasia, these data suggest that they are at risk for its development.

The reduced level of apoptosis present in the colonic crypts of individuals with a history of colorectal neoplasia shown in the above example demonstrates the utility of measurement of the extent of apoptosis for the purposes of the present invention. By establishing normal and abnormal ranges for AI from patients who have had, who have, and are at risk for the development of colorectal neoplasia, the results from a biopsy may be compared to the ranges to categorize the results. If the patient has no history of colorectal neoplasia, the results may be used to indicate that the patient is at risk for its development, and appropriate dietary modification or administration of chemopreventive agents may be initiated. The results of the assessment may indicate that more frequent colorectal examinations be performed. If a colorectal neoplasm is found and surgically removed, and may be followed up with chemotherapy, and the response of the patient's colonic cells to the therapy monitored by this method. In accordance with the present method, the assessment may be used to monitor an individual's responsiveness to prevention or intervention therapy: the change in the AI of biopsy specimens taken prior to and after initiation of therapy will be used to determine whether an individual is responding to a particular therapy, or the reason for no clinical response is lack of a change in AI as a result of therapy. The change in AI may be useful for both chemopreventive measures in patients with a demonstrated risk for the development of colorectal neoplasia, or for patients with demonstrated neoplasia undergoing chemotherapy. Determining at an early stage that a chemotherapeutic is ineffective is of enormous benefit to the patient in arriving at an effective course of therapy.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for determining whether an individual is at risk for the development of colorectal neoplasia, said method comprising the steps of:

i) gathering a sample of normal colonic tissue or normal colonic cells from said individual;

ii) determining the percentage of cells from said sample that are apoptotic or display DNA fragmentation in the mucosal crypt or in one of its subdivisions or compartments;

iii) comparing said percentage to a normal percentage range established for individuals at no risk for the development of colorectal neoplasia, said normal percentage range established by determining the percentage of cells that are apoptotic or display DNA fragmentation in the mucosal crypt or in one of its subdivisions or compartments from said individuals at no risk for the development of colorectal neoplasia; and iv) correlating said percentage below said normal percentage range with the determination that said individual is at risk for the development of colorectal neoplasia.

2. The method of claim 1 wherein said determining the percentage of cells from said sample that are apoptotic or display DNA fragmentation is performed by TdT-mediated dUTP biotin nick end labeling (TUNEL) methodology.

* * * * *